United States Patent [19]

Messier et al.

[11] Patent Number: 5,681,740
[45] Date of Patent: Oct. 28, 1997

[54] APPARATUS AND METHOD FOR STORAGE AND TRANSPORATION OF BIOARTIFICIAL ORGANS

[75] Inventors: Kenneth A. Messier, Cranston, R.I.; Nicholas F. Warner, Belmont, Mass.

[73] Assignee: CytoTherapeutics, Inc., Providence, R.I.

[21] Appl. No.: 463,658

[22] Filed: Jun. 5, 1995

[51] Int. Cl.$^6$ ............................ C12M 1/24; A01N 1/02
[52] U.S. Cl. .................... 435/284.1; 435/304.1; 435/304.2; 435/307.1; 206/438
[58] Field of Search .................. 435/1.1, 1.2, 1.3, 435/284.1, 288.1, 288.2, 303.1, 304.1, 304.2, 307.1, 809; 422/102; 206/438, 439, 205, 5.1; 600/36; 604/890.1, 891.1, 892.1, 403, 415; 424/424, 425, 93.1, 93.7

[56] References Cited

U.S. PATENT DOCUMENTS

| | | | |
|---|---|---|---|
| 2,051,349 | 8/1936 | Goldberg | 206/438 |
| 2,880,856 | 4/1959 | Albrecht | 206/438 |
| 3,950,227 | 4/1976 | Efthymiou | 435/304.1 |
| 4,061,134 | 12/1977 | Samuels et al. | 206/438 |
| 4,211,325 | 7/1980 | Wright | 206/438 |
| 4,377,077 | 3/1983 | Granlund | 435/307.1 |
| 4,501,360 | 2/1985 | Levy et al. | use 435/307.1 |
| 4,736,850 | 4/1988 | Bowman et al. | 206/570 |
| 4,844,242 | 7/1989 | Chen et al. | 206/438 |
| 4,892,538 | 1/1990 | Aebischer et al. | 604/891.1 |
| 4,951,482 | 8/1990 | Gilbert . | |
| 5,002,661 | 3/1991 | Chick et al. | 210/192 |
| 5,106,627 | 4/1992 | Aebischer et al. | 424/424 |
| 5,156,844 | 10/1992 | Aebischer et al. | 424/424 |
| 5,158,881 | 10/1992 | Aebischer et al. | 435/182 |
| 5,182,111 | 1/1993 | Aebischer et al. | 424/424 |

FOREIGN PATENT DOCUMENTS

| | | | |
|---|---|---|---|
| 1159534 | 6/1985 | U.S.S.R. | 435/284.1 |
| 1650694 | 5/1991 | U.S.S.R. | 435/304.1 |
| 85/02975 | 7/1985 | WIPO | 435/284.1 |
| WO 91/00119 | 1/1991 | WIPO . | |
| WO 91/03934 | 4/1991 | WIPO . | |
| WO 91/18575 | 12/1991 | WIPO . | |
| WO 92/07525 | 5/1992 | WIPO . | |
| WO 92/19195 | 11/1992 | WIPO . | |
| WO 93/03901 | 3/1993 | WIPO . | |
| WO 93/21902 | 11/1993 | WIPO . | |
| WO 95/01203 | 1/1995 | WIPO . | |

OTHER PUBLICATIONS

Aebischer et al., "Transplantation in Humans of Encapsulated Xenogeneic Cells Without Immunosuppression," *Transplantation*, vol. 58, pp. 1275–77 (1994).

Primary Examiner—William H. Beisner
Attorney, Agent, or Firm—Fish & Neave; Ivor R. Elrifi; Pablo D. Hendler

[57] ABSTRACT

Bioartificial organ storage and transport apparatus having a media storage container. The apparatus is designed to securely maintain a bioartificial organ within the container in a sealed environment. The apparatus may also allow for gas exchange and media exchange to ensure the viability of the bioartificial organ. In addition, the apparatus may use a secondary container and cap, designed to allow access to the media storage container and allow for gas exchange and media exchange.

3 Claims, 5 Drawing Sheets

APPARATUS AND METHOD FOR STORAGE AND TRANSPORATION OF BIOARTIFICIAL ORGANS

FIELD OF THE INVENTION

The present invention relates to an apparatus and method for storing and transporting bioartificial organs ("BAOs"). The apparatus of this invention is designed to contain the BAO so that the BAO is maintained under suitable culture conditions. This ensures the viability and sterility of the BAOs until implantation into the recipient. Further, the apparatus of this invention is designed to minimize damage to the BAO during transportation.

BACKGROUND OF THE INVENTION

BAOs are devices which may be designed for implantation in a recipient or which can be made to function extra-corporeally. BAOs contain living cells or tissue, which produce a biologically active molecule or provide a needed biological function to an individual. Generally, BAOs also contain a semipermeable membrane, which allows for the diffusion of nutrients to the cells and also allows the secreted cellular products and waste materials to diffuse away from the cells. In some cases, the membrane may serve to also immunoisolate the cells by blocking the cellular and molecular effectors of immunological rejection. The use of immunoisolatory membranes allows for the implantation of allo and xenogeneic cells into an individual without the use of immunosuppression. If biologically active molecules are released from the isolated cells, they pass through the surrounding semipermeable membrane into the recipient's body. If metabolic functions are provided by the isolated cells, the substances to be metabolized enter the BAO from the recipient's body through the membrane to be acted on by the cells.

A variety of types of membranes have been used in the construction of BAOs. Generally, the membranes used in BAOs are either microporous or ultrafiltration grade membranes. A variety of membrane materials have been suggested for use in BAOs, including PAN/PVC, polyurethanes, polysulfones, polyvinylidienes, and polystyrenes. Typical membrane geometries include flat sheets, which may be fabricated into "sandwich" type constructions, having a layer of living cells positioned between two essentially planar membranes with seals formed around the perimeter of the device. Alternatively, hollow fiber devices may be used, where the living cells are located in the interior of a tubular membrane. Hollow fiber BAOs may be formed step-wise by loading living cells in the lumen of the hollow fiber and providing seals on the ends of the fiber. Hollow fiber BAOs may also be formed by a coextrusion process, where living cells are coextruded with a polymeric solution which forms a membrane around the cells.

A common characteristic of the membranes useful in BAOs is that they are relatively thin walled and are porous in nature. These membranes tend to be fragile and can be damaged during fabrication and subsequent handling, transport and implantation of the BAO.

BAOs have been described, for example, in U.S. Pat. Nos. 4,892,538, 5,106,627, 5,156,844, 5,158,881, and 5,182,111, and PCT Application Nos. PCT/US 94/07015 and WO 92/19195, all of which are incorporated herein by reference. See also Published PCT Application Nos. WO 93/03901 and WO 91/00119.

In addition to living cells and semipermeable membranes, BAOs may contain other components. For example, PCT publication WO 92/19195 discloses implantable immunoisolatory biocompatible vehicles having a hydrogel matrix for enhancing cell viability and having a tether which aids in retrieval of the device. PCT publication WO 91/00119 discloses cell-containing membrane implants having external supports for connecting a plurality of cell-containing tubular membranes. PCT application WO 93/21902 teaches implantable devices having rigid or semi-rigid support structures. PCT application US 94/07015 teaches implantable devices having ports to facilitate cell introduction and provide for reliable, cell-tight seals. Issued U.S. Pat. No. 5,002,661 teaches an intravascular artificial pancreatic perfusion device having a housing for containing living cells suspended in a matrix.

Implantable BAOs may be introduced into a recipient in one of two ways: (1) implantation of an empty BAO semipermeable membrane device followed by in situ addition of the living cells, or (2) implantation of pre-filled, cell-containing devices. In many instances, the latter approach is desirable, in part due to the fact that the potential implant site may not be readily accessible for in situ filling. Performance of pre-filled devices may also be more readily characterized in vitro. However, the storage and transport of pre-filled devices presents a number of problems.

First, once fabricated, the BAO must be maintained under suitable culture conditions to ensure the viability of the cells and the sterility of the devices until the time the BAO is to be implanted. In fact, in order to ensure that the BAOs are functional and sterile prior to implantation, the devices are held and tested for a period of many days. Sufficient testing may require holding periods of approximately 17–24 days. However, holding periods longer than even a short period of time, such as about one week, require that the fluid media surrounding the BAO be replenished periodically to provide a fresh source of nutrients and to remove waste products from the encapsulated cells. Additionally, the fluid media will require sufficient dissolved gases, including oxygen, to maintain cell viability. It will be recognized that the nutrient and other requirements of the BAO will depend upon many factors, including the type of cells encapsulated, the metabolic activity of the cells, and the number and loading density of the cells.

For example, bovine adrenal chromaffin cells have been used in BAOs for implantation into human subjects for the treatment of chronic pain. Aebischer et al., "Transplantation in Humans of Encapsulated Xenogeneic Cells Without Immunosuppression," *Transplantation*, vol.58, pp.1275–77 (1994). These BAOs have been shown to secrete several analgesic compounds, including norepinephrine, met-enkaphalon, octapeptide, and epinephrine. The BAOs are incubated in serum-free culture medium during the holding period. To maintain the release capability of analgesic substances, it is necessary to replenish the medium after about twelve days. Typically after replenishment, a three day hold is performed to ensure that the BAOs remain sterile. The BAOs are cleared for shipping after day 15, and may be shipped up to day 20. At day 20, the media must be replenished again, and a three day hold is again required to check for sterility. Consequently, any storage system for BAOs must allow for easy access to the storage media to feed the BAOs.

Another problem encountered with the use of pre-filled BAOs is that since they are generally not fabricated at the location where they are to be used, it is necessary to transport the BAOs to their implantation destination. For example, prior to the instant invention, BAOs were often hand carried to the implantation destination in standard labware, such as flasks or polypropylene screw cap tubes. Since the BAOs tend to be somewhat fragile, primarily due to the porous nature of the encapsulating membrane, occasional damage to the BAO has been observed during transit when shipped in standard labware.

Various packaging systems have been described for storage and transportation of body organs and tissue. See, e.g., Tubo, Published PCT Application No. WO 91/18575 ("Tubo"); and Krasner, Published PCT Application No. WO 91/03934 ("Krasner"). Tubo refers to a container for storage and distribution of cultured epithelial skin wound dressings. The container comprises a presterilized housing supporting the wound dressing in a sodium bicarbonate medium, and a cover having a gas-tight seal to the housing. In Tubo, the gas-tight seal is essential to the container since the sodium bicarbonate medium requires 10% $CO_2$ for maintenance of proper pH.

Krasner refers to a container for the storage and transport of body organs such as severed limbs, or for the storage and preservation of bone graft material. In Krasner, the body organs or bone graft material are dropped into a net or basket which is suspended in a reservoir of preservation solution. The body organs or bone graft material are not secured in the container so as to prevent undue contact with the container during transportation.

Bowman et al., U.S. Pat. No. 4,736,850, describe a kit for harvesting cells from an excised vein. The cell harvesting kit includes a packaging container having three internal trays to support the components needed for cell-harvesting as well as the excised vein. The kit is not designed to hold fluid media nor store the excised veins for anything other than a short period of time. In addition, the excised veins are not secured in the packaging container so as to prevent undue contact with the container during transportation.

It is important that the exposure of the cell-containing portions of the BAO to air be carefully controlled. Prolonged exposure of the BAO to air will result in a drying out of the device which may be deleterious to cell viability. Preferably, the BAO is totally immersed in fluid media while secured in the storage and transport apparatus, regardless of the orientation of the apparatus.

A need exists for an apparatus to store and transport BAOs without substantially compromising the BAO's integrity, sterility and cell viability.

SUMMARY OF THE INVENTION

The present invention provides an apparatus and method for the storage and transportation of BAOs that substantially preserves the BAO's integrity, sterility and cell viability. The apparatus comprises a media storage container which bathes one or more BAO in a suitable volume of media, a means for securing the BAOs within the media storage container, preferably such that the BAOs remain immersed in liquid media regardless of the orientation of the BAO, and a means for sealing the media storage container designed to provide a substantially fluid-tight seal. The securing means is designed to prevent damage to the BAO resulting from undue turbulence or physical contact with other elements of the media storage container.

Where the BAO is to be kept in the fluid media for more than a short period of time (i.e. approximately one week), the apparatus preferably has a media exchange means and a gas exchange means to maintain the viability of the cells in the BAO. The fluid exchange means allows for the provision of fresh media and removal of waste products, while the gas exchange means allows for the introduction of oxygen to the media to sustain the living cells in the BAO.

The apparatus also optionally comprises a secondary container which surrounds the media storage container. The use of a secondary container minimizes handling of the media storage container, thus reducing the risk that sterility of the BAO may be compromised. The secondary container also facilitates the introduction of the bioartificial organ to a sterile field at the time of implantation.

DETAILED DESCRIPTION OF THE INVENTION

In order that this invention may be more fully understood, the following detailed description is set forth.

The present invention provides an apparatus and method for the storage and transportation of BAOs. Generally, the apparatus comprises a media storage container which holds a volume of fluid media, a means for securing the BAOs within the media storage container, and a means for sealing the media storage container designed to provide a substantially fluid-tight seal. Preferred embodiments further comprise a media exchange means and a gas exchange means to maintain the viability of the cells in the BAO.

The apparatus also optionally comprises a secondary container which surrounds the media storage container. Preferably, the secondary container has means for accessing the exchange means of the inner container (the media storage container). Additionally, the secondary container may have means for exchanging moisture from the inside of the secondary container to the external atmosphere so as to prevent the excessive buildup of humidity inside the secondary container.

More particularly, the BAO storage and transport apparatus of this invention comprises a media storage container 10 and a cap 12. Typically, media storage container 10 has well 14 to facilitate media exchange. Well 14 may have any suitable design, including a gutter formed around the bottom of media storage container 10 and/or a low spot on the bottom. The presence of such a well or low spot provides a channel to direct air bubbles away from the BAO if media storage container 10 is inadvertently transported or stored in an upside down orientation. Preferably, media collection well 14 should be located away from the fragile BAO semipermeable membrane to ensure that the BAO is not damaged during any media exchange procedures.

In one embodiment, media storage container 10 has a convex base 16. In addition, the circumference of base 16 forms well or gutter 14 around the bottom of media storage container 10.

Securing means 20 for securing the BAO within media storage container 10 may be attached to the interior of media storage container 10 or the bottom of cap 12. Securing means may also comprise an insert which fits into media storage container 10. Preferably, securing means 20 are attached to base 16. Under normal operating conditions, securing means 20 keeps the BAO submerged in fluid media so that the BAO is not subject to undue contact with any system component other than the securing means.

Any suitable securing means may be used to secure the BAO. The skilled artisan will appreciate that the exact design of securing means 20 will vary according to the design of the BAO.

As stated above, BAOs are devices which contain living cells or tissues encapsulated in a semipermeable membrane. The membrane may be sealed in a variety of ways, such as with caps, glue or heat sealing, to form either one cell compartment or multiple compartments. In addition, BAOs may also have means for retrieving the device after implantation, such as a tether attached to a sealed end.

Preferably, securing means 20 will not physically compress the semipermeable membrane portions of the BAO. It is contemplated that the securing means makes contact with the BAO at a non-membrane portion of the BAO, such as tethers, supports, seals, or connectors.

Securing means 20 should provide for substantially unrestricted flow of fluid media over the BAO, which allows for the free exchange of nutrients and waste products. Preferably, securing means 20 allows the BAO to be free-floating in the media.

Figure 1:
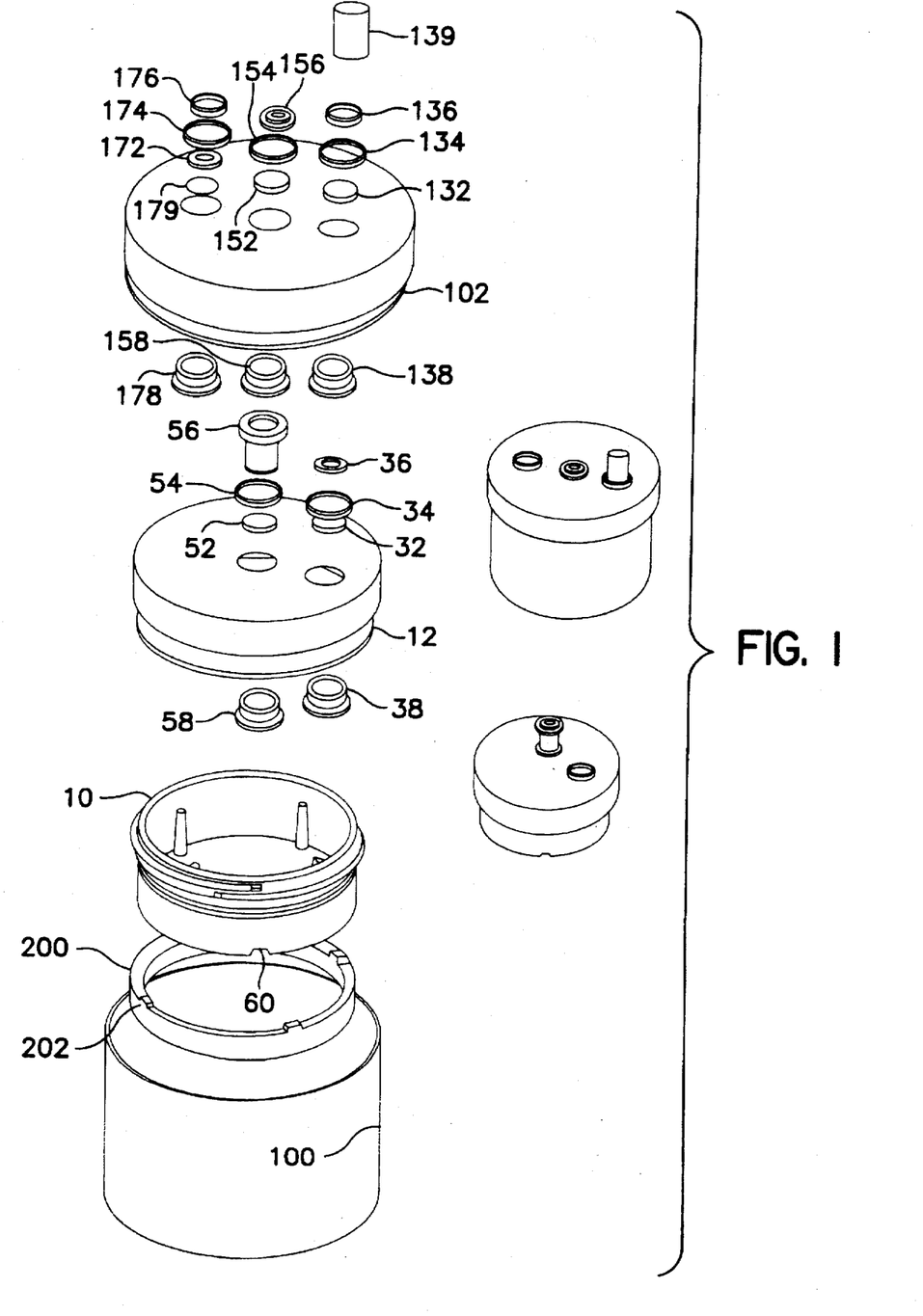
FIG. 1 shows a preferred BAO storage and transport apparatus. The apparatus comprises a media storage container 10 and cap 12. Also shown is secondary container 100 and secondary cap 102.
Figure 2:
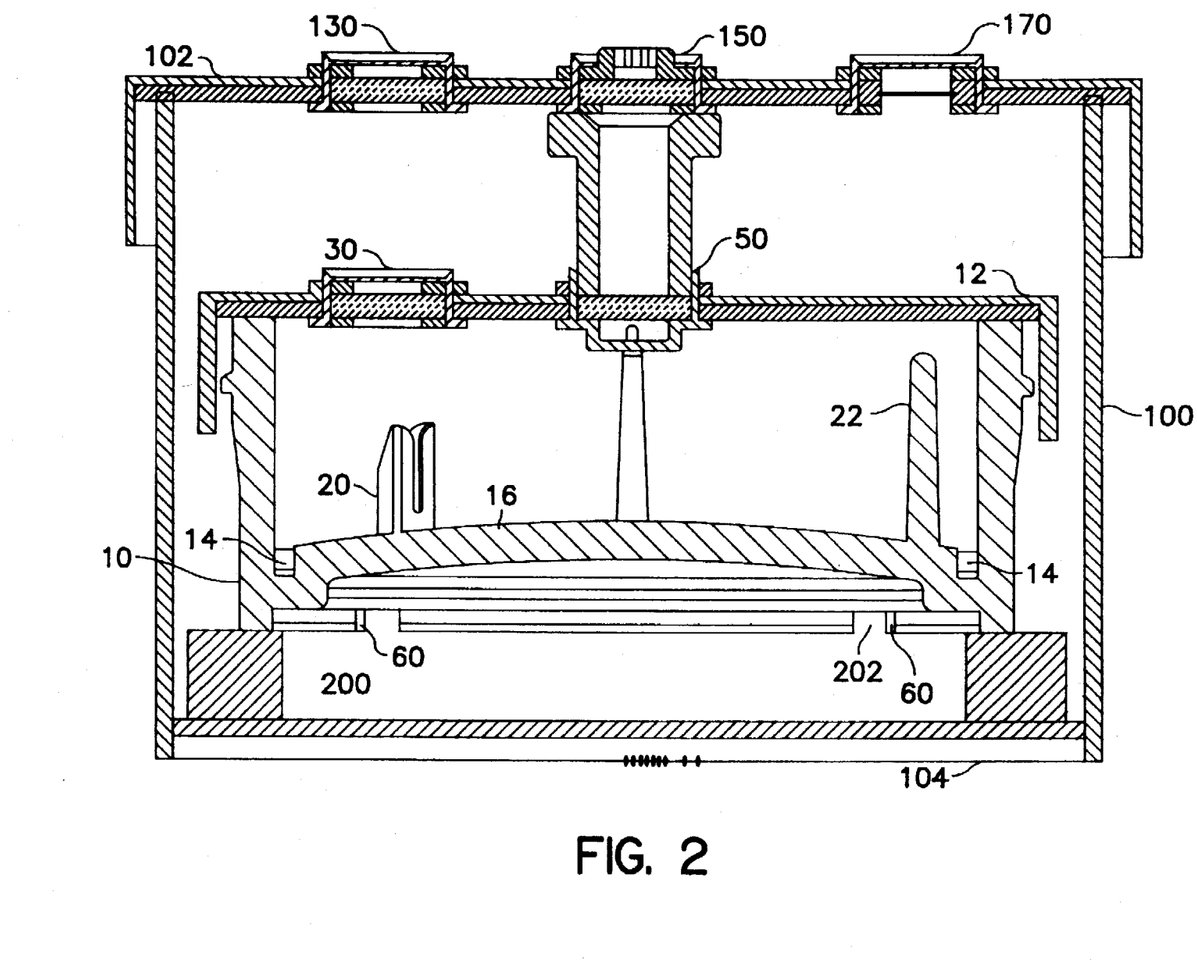
FIG. 2 shows a cross-sectional view of a BAO storage and transport apparatus comprising media storage container 10 and cap 12, contained within secondary container 100 and secondary cap 102.

In a preferred embodiment shown in FIGS. 1 and 2, the securing means comprises prongs 20 and post 22. As shown, prongs 20 and post 22 are attached to base 16 of media storage container 10. It is contemplated that prongs 20 and post 22 may be positioned on base 16 to accommodate various sized BAOs.

In the preferred embodiment, the prongs 20 and post 22 are designed to engage a BAO capped at one end with a hub-sealed fitting having a tether attached to the cap. Hub-sealed BAOs are taught in PCT/US 94/07015. The hub-sealed BAO is secured by positioning the tether in prong 20 such that the non-membrane portion of the BAO (e.g., hub-sealed cap) is flush with the external surface of prong 20, and then wrapping the tether around post 22. The BAO is thus secured at one end only, with the fragile semipermeable portion free-floating in the central portion of media storage container 10. The BAO may be further secured to holding prong 20 and/or post 22 by the use of appropriate clips or slots, or other suitable means.

It is also contemplated that prongs 20 may engage and secure BAOs of other designs. For example, BAOs which have external non-membrane features (e.g., supports for connecting a plurality of cell-containing membranes) may be secured within the media by attaching prongs 20 around the non-membrane portion.

In addition, the securing means may be designed to secure a BAO at more than one location. This may be accomplished by using any combination of prongs 20 and/or posts 22 so long as the integrity of the functional membrane portion of the BAO is not compromised. For example, where the BAO has non-membrane portions at both ends of the BAO (e.g., end supports and sealing caps as described in published PCT Application No. WO 91/00119), the prongs 20 may be aligned so that each non-membrane portion may be inserted through the slot of a different prong 20.

Cap 12 provides a substantially fluid-tight seal when sealingly engaged with media storage container 10. In the preferred embodiment, when cap 12 is engaged, media storage container 10 is invertible such that the BAO remains submerged in the media and does not come into contact with air bubbles which will tend to accumulate in the media collection well or low spot. This ensures that during transportation, if the container is inadvertently inverted, the BAO will not dry out. Preferably, the cap has a liner (e.g., a compressible material such as silicone elastomer) which aids in the formation of a fluid-tight seal. Additionally, the cap may be designed so that a portion of it extends into the media cavity thereby causing a volume of the media to expel from the container. This serves to minimize the formation of air pockets within the media-filled storage and transport apparatus when sealed. This ensures that the BAO is completely surrounded by fluid media during storage and transport.

The liner may be formed by a layered construction approach in which a layer of silicone is placed between two layers of other suitable polymers (e.g., polypropylene or fluoroethylenepropylene). The liner may be fixed to the cap by any suitable means, such as ultrasound welding. Where the liner is formed by layered construction, the inner layer of the liner, that which makes contact with the cap, will be made of the same material as the cap in order to facilitate ultrasound welding. The outer layer may be of any suitable material which will be low friction and sufficiently durable to form a fluid-tight seal. For example, fluorinated perfluoroethylene polypropylene (FEP), a copolymer of hexafluoropropylene and tetrafluoroethylene, is a suitable material for the low-friction layer of the liner. FEP has very similar properties as polytetrafluoroethylene (PTFE), but it is more stable during gamma irradiation sterilization than is PTFE.

Where a liner is used, it is preferred that media storage container 10 has a sealing rim around its outer perimeter so that when cap 12 is engaged to the container, the sealing rim is embedded into the compressible liner to form the fluid-tight seal.

One embodiment of cap 12 is a lid which is heat-sealed to the top of media storage container 10. Heat sealing equipment is well known. Where a liner is used, it may be comprised of spun-bonded olefin, paper, aluminum foil, or similar materials known in the art. In this embodiment, the liner contains a resin which binds the liner to container 10 when heat is applied.

Figure 3:
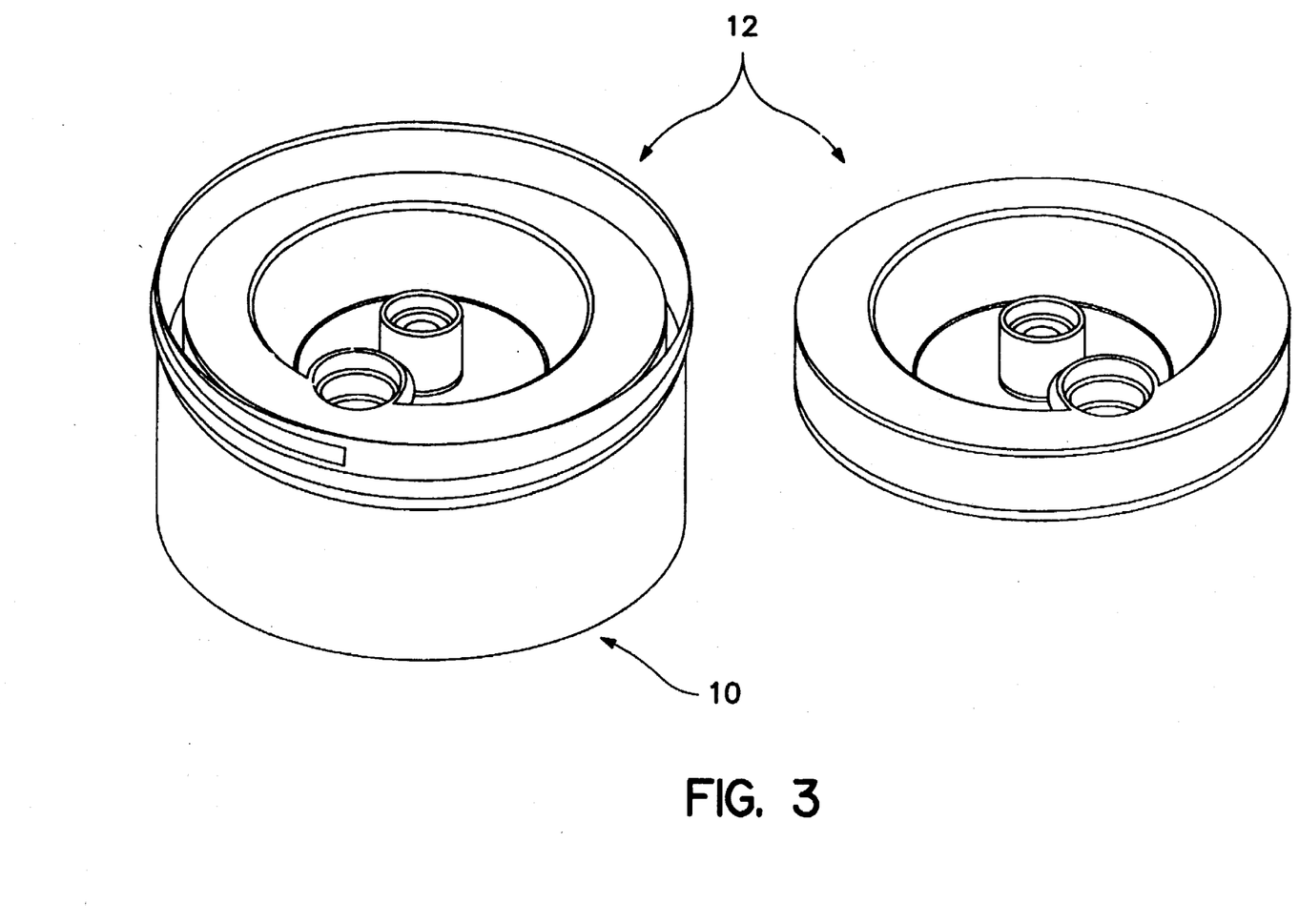
FIG. 3 shows a BAO storage and transport apparatus comprising media storage container 10 and an alternative embodiment of cap 12.

In another embodiment, cap 12 is a threaded lid which engages mating threads on the top of media storage container 10. In a further embodiment shown in FIG. 3, cap 12 is a threaded lid which has a recessed region which expels media from media storage container 10 as the cap engages the mating threads on the top of the container. This minimizes the formation of air pockets within the media container when sealed, and thus further ensures that the BAO is completely surrounded by fluid media during storage and transport.

A preferred embodiment of the storage and transport apparatus, shown in FIGS. 1 and 2, further includes gas exchange means 50 and media exchange means 30.

The ability to exchange gas to the media aids in maintaining the viability of the living cells within the BAO. Alternatively, sufficient oxygen may be introduced into the packaging system by saturating the media prior to engaging the sealing means, or by using a breathable liner.

As shown, gas exchange means 50 is a resealable port which allows for gaseous communication between the outside of a sealed media storage container and its interior. The port may be resealed by any suitable method, such as a cap, plug, or preferably self-sealing septum 52. Such septa are well known in the art.

In the embodiments using a self-sealing septum, to allow gas exchange, a hollow needle or a suitable alternative is inserted through septum 52 into the media in media storage container 10. The needle preferably contains a microbial filter (e.g., 0.22 micron PTFE filter in a polypropylene housing) to avoid contamination of media storage container 10, and thus the BAO, with contaminants in the introduced gas.

Preferably, gas exchange means 50 also includes a stop member which limits the extent to which a needle may be inserted into media storage container 10. The stop member prevents the needle from coming into contact with the BAO, and thus preventing accidental perforation of the BAO.

Media exchange means 30 is similar in design to gas exchange means 50. For example, media exchange means 30 may also comprise a resealable port for accessing media. Preferably, media exchange means 30 accesses media collection well 14. Media may be removed from or introduced into media storage container 10 using a needle, tube, or other suitable methods.

Preferably, media exchange means 30 includes self-sealing septum 32, which is aligned directly over media collection well 14. To exchange media, a needle is inserted through septum 32 such that the needle opening is positioned in the well. The media in the well is then aspirated and removed from the system. Fresh media may be introduced in a similar fashion. Preferably during media exchange, the media passes through a suitable filter to prevent introduction of any contaminants to media storage container 10. After media exchange occurs, the needle is removed and septum 32 self-seals to form a fluid-tight seal.

Where gas exchange means 50 and media exchange means 30 use self-sealing septa, a preferred embodiment uses snap fittings to house the septa. For example, gas exchange snap fit base 58 and media exchange snap fit base 38 are inserted through the bottom of the appropriate ports in cap 12 such that a portion of snap fit bases 58 and 38 extend through the top of cap 12. Septa 52 and 32 are then inserted into snap fit bases 58 and 38. Containing rings 54 and 34 snugly fit around the portion of the snap fit bases 58 and 38 which extend through the top of cap 12.

Snap fit inserts 56 and 36 then mate to the tops of snap fit bases 58 and 38, respectively. The snap fit bases and snap fit inserts are designed to pull toward each other when mated, thus ensuring a fluid-tight seal around septa 52 and 32 and the cap liner.

The snap fit housings for either or both gas exchange means 50 or media exchange means 30, may also serve as a handle for media storage container 10. As shown in FIG. 1, snap fit insert 56 functions as a handle. The components for these fittings can be fabricated by machining, injection molding, or other common techniques. As an alternative to snap fittings, inserts may be ultrasonically welded on to cap 12.

In another embodiment, media may be supplied by one or more additional containers integral to media storage container 10. In this embodiment, spent media is drained from media storage container 10 via tubing that connects media storage container 10 to a spent media reservoir. Fresh media in introduced from a fresh medium reservoir in fluid connection with media storage container 10. Most preferably, the media exchange reservoirs can be disconnected from media storage container 10 without compromising the sterility of its contents. Once disconnected, the reservoirs may be drained or refilled, as appropriate, and then reconnected to media storage container 10 in a sterile fashion. Such procedures are known in the art.

FIGS. 1 and 2 additionally show secondary container 100 and secondary cap 102, which enclose media storage container 10 and cap 12. Secondary cap 102 provides a substantially fluid-tight seal when sealingly engaged with secondary container 100. In one embodiment, secondary cap 102 is a threaded lid which engages mating threads on the top of secondary container 100. Preferably, secondary cap 102 has a liner, as described above for cap 12.

In addition, preferably secondary cap 102 has means for accessing gas exchange means 50 and media exchange means 30 as well as means for releasing humidity. These accessing means and humidity exchange means are similar in design to exchange means 50 and 30 on cap 12 of media storage container 10, but may have any other suitable design.

A preferred embodiment having gas accessing means 150 and media accessing means 130 is shown in FIG. 2. As shown, accessing means 150 and 130 have self-sealing septa 152 and 132 in snap fit housings (i.e., bases 158 and 138, containing rings 154 and 134, top inserts 156 and 136).

Gas accessing means 150 is aligned with gas exchange means 50 and media accessing means 130 is aligned with media exchange means 30, such that a needle, or other suitable instrument, may be inserted from the external environment through septa of the secondary container and then through the septa of the media storage container thus penetrating the media storage environment so as to allow for gas and/or media exchange. In a preferred embodiment, the bottom of media storage container 10 has a key mechanism 60, which fits into a mating base 200. Key mechanism 60 ensures that the accessing means 150 and 130 of secondary cap 102 are aligned over the exchange means of cap 12.

In addition, key mechanism 60 allows an operator to align media exchange means 30 of cap 12, with the media collection well 14 of the base of media storage container 10. This is accomplished by placing media storage container 10 on a base plate which is similar in design to mating base 200.

Furthermore, where cap 12 is a threaded lid, key mechanism 60 also facilitates the attachment or detachment of cap 12 without extensive handling of media storage container 10. Key mechanism 60 allows an operator to secure or remove cap 12 simply by fitting media storage container 10 into a mating base similar to mating base 200 and applying a torque to cap 12. Reduced handling of media storage container 10 is desireable because of the reduced potential for contamination.

In a preferred embodiment, shown in FIGS. 1 and 2, the storage and transport apparatus further includes humidity exchange means 170 which is similar in design to gas exchange means 50. The humidity exchange means is positioned on secondary cap 102 and comprises septum 172 having a hole into which breathable liner 179 is positioned. Breathable liner 179 may be, for example, a nylon 0.22 micron porosity membrane disk. A nylon membrane is preferred as it is capable of withstanding sterilization procedures, such as gamma irradiation. A 0.22 micron porosity is preferred to prevent microbial contaminants from entering the inside of the secondary container.

Humidity exchange means 170 allows for moisture release and pressure equalization during transport in order to prevent condensation from forming on the inside of the secondary container. Humidity exchange is desireable as the container may be stored in a humidified atmosphere incubator. Without humidity exchange means 170, humidity may condense and remain within the secondary container as the temperature drops from about 37° C. in the incubator to room temperature during shipping.

Figure 5:
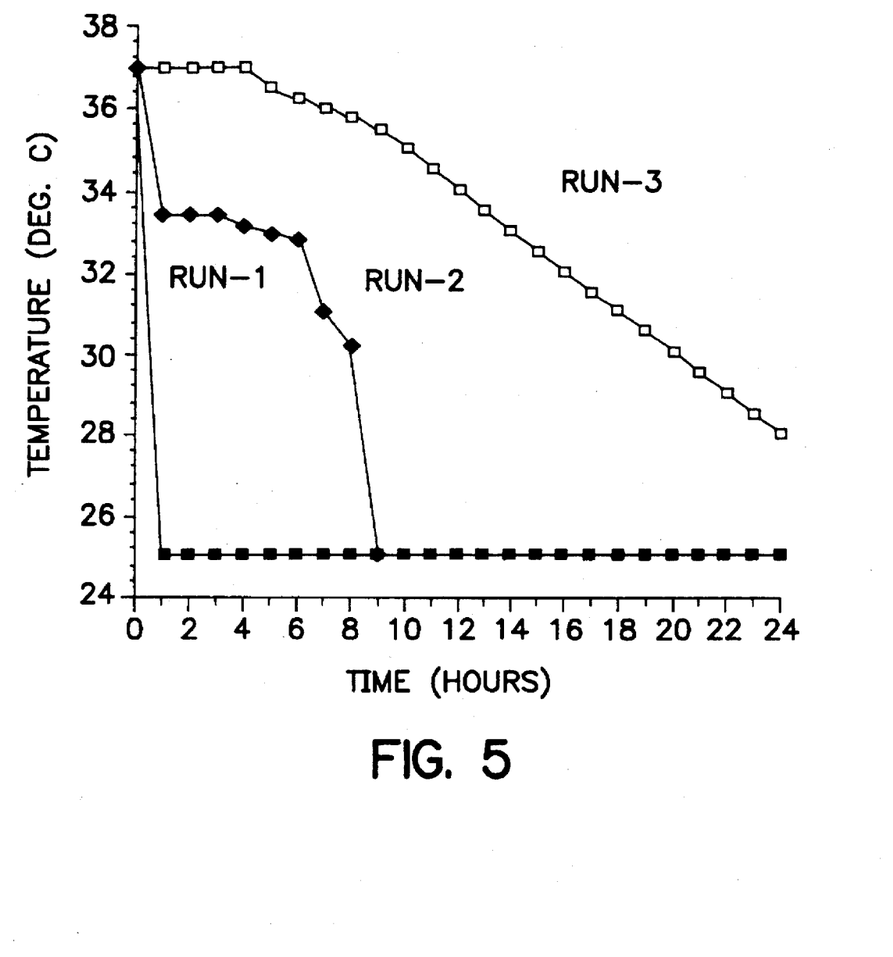
FIG. 5 shows the effects of temperature and time on condensation within a BAO storage and transport apparatus during shipping.

In FIG. 5, the effect of temperature loss on condensation is graphically represented. Each of the three runs shown were carried out on a storage and transport apparatus of this invention in which the secondary container included humidity exchange means comprising a nylon 0.22 micron porosity membrane disk positioned on the secondary cap within a septum having a hole with an inner diameter of 0.312 inches. The initial temperature of the apparatus for each run was about 37° C.

Run-1 represents "quick cool" conditions in which the temperature of the apparatus was dropped rapidly from about 37° C. to about 25° C. in one hour. Under such conditions condensation appeared, but over time the inside of the secondary container will dry out as the condensed moisture evaporates through the membrane disk.

Run-2 represents "slow cool" conditions in which the temperature of the apparatus was controlled. Under these conditions, the membrane disk appears to have prevented condensation from forming within the secondary container during the test period.

Run-3 represents simulated operating conditions (actual thermal and time conditions expected during a routine commercial shipment). During this run, the container was maintained at simulated shipping conditions for a period of about 8 hours after which time, the container was exposed to "fast cool" conditions. Condensation did not visibly appear during the simulated shipment period. As with the "slow cool" run, the membrane disk appears to have prevented condensation from forming within the secondary container. Only after the apparatus was exposed to "fast cool" conditions, did condensation appear.

The snap fit housings for gas accessing means 150, media accessing means 130 and humidity exchange means 170, may be constructed in a similar fashion as gas exchange means 50 and media exchange means 30. Snap fit bases 158, 138 and 178 are inserted through the bottom of appropriate ports in secondary cap 102. Septa 152, 132 and 172 are then inserted into snap fit bases 158, 138 and 178, respectively. With respect to humidity exchange means 170, septum 172 has a hole into which breathable liner 179 is inserted. Containing rings 154, 134 and 174 are fixed around snap fit bases 158, 138 and 178, respectively, to secure the snap fittings to secondary cap 102. Finally, snap fit inserts 156, 136 and 176 are mated to the top of the snap fit bases 158, 138 and 178, respectively. It is preferred that snap fit insert 156 include a needle holder arrangement while snap fit insert 136 provides for septa lid 139.

Alternatively, as with exchange means 30 and 50 of cap 12, the snap fittings used with accessing means 130 and 150 as well as humidity exchange means 170, may be replaced with inserts which are ultrasonically welded on to cap 102.

Secondary container 100 minimizes the need to handle primary container 10 once the BAO and the media are initially loaded. Subsequent gas and media exchanges can be performed through both containers with minimal disturbance of the storage and transport apparatus, and with a substantially reduced risk of contamination of the BAO.

Upon delivery to the implantation destination, secondary container 100 can be opened outside the sterile field, and media storage container 10 can be delivered into the sterile field, thus reducing the potential for the introduction of unwanted biological contaminants into the sterile field.

If secondary container 100 is used, slotted mating base 200 may take the form of a disk attached inside the base of secondary container 100, for example, by ultrasonic welding. Slotted mating base 200 has several locking tabs 202 along its upper rim. These locking tabs 202 mate with key mechanism 60, which are shown in FIGS. 1 and 2 as a series of slots on the bottom of media storage container 10. When media storage container 10 is inserted in secondary container 100, the slots receive locking tabs 202. Alternatively, the secondary container and the slotted mating base may be manufactured as a single unit using, for example, injection molding.

Media storage container 10 should fit snugly in secondary container 100 in order to prevent movement of the media storage container which could result in damage to the BAO. This snug fit may be readily achieved by suitable design of the height of the gas exchange means 50.

Any suitable material may be used in the fabrication of the storage and transport apparatus, including metal, such as stainless steel, aluminum alloys, or titanium based materials, or ceramics, such as silica or alumina based ceramics, available from, e.g., Coors Company, Boulder, Colo. Any material may be used that is capable of withstanding common methods of sterilization, such as irradiation (i.e. gamma irradiation), chemical methods (i.e. ethylene oxide sterilization), and autoclaving.

If the sterilization method is gamma irradiation, the materials chosen, if necessary, should contain stabilizers to gamma radiation to prevent discoloration or deterioration. Commercially available polycarbonate polymers have such stabilizers. Such polymers are typically colored (e.g. tinted purple) prior to gamma sterilization. Upon exposure to gamma radiation, the polymers may turn yellowish in color; however, if properly gamma stabilized, these colored polycarbonate polymers will revert back to their natural tint after a short storage period.

In addition, the materials should be sufficiently durable to withstand the rigors of shipping and handling. Further, the materials should be sufficiently non-toxic to living cells so as not to produce appreciable detrimental effects to the BAOs. Preferably, the materials should be USP Class 6 tested.

While reusable materials are contemplated, preferably, the materials are disposable.

It is also preferable that at least some of the components of the storage and transport apparatus are optically clear. This will allow for easy discovery of visible contamination of the BAO. Examples of visible contamination include turbidity and discoloration of the fluid media.

Preferably, media storage container 10 and secondary container 100 are constructed of optically clear materials such as glass, or a suitable polymer. Useful polymers include any durable, non-fragile material such as polycarbonate, polyphenylene oxide, polyesters, polyetheramide, polyethylene terephthalate, polyethylene co-glycol terephthalate, and similar resins. More preferred are polycarbonate polymers since: (1) they are more durable than some other suitable materials, (2) are available in USP class 6 grades, and (3) are thermoformable.

The containers and caps of this invention may be manufactured by any appropriate technique. For example, they may be constructed by injection molding or other thermoforming methods. Alternatively, they may be machined, or assembled using bonding techniques such as ultrasonic welding. The preferred method of manufacture is a thermoforming process such as injection molding, as this process readily accommodates the production of complex shapes.

Containing rings which are produced from polycarbonate materials by machining or injection molding have stress lines which are amplified by exposure to gamma irradiation during sterilization. It is desireable to remove the stress lines in order to ensure the toughness of the plastic. Annealing may be performed to reduce the stress imbalance. Exposing the machine or molded rings to a temperature of about 250° C. for approximately 10 minutes and then cooling slowly (over several hours) to prevent thermal shock, accelerates the stress relaxation process that occurs in all thermoplastics. By annealing, the internal stresses are reduced which improves the dimensional and performance stability of the parts.

When shipping the devices, care must be taken to minimize the physical rigors of transport. As a result, a tertiary container for shipping may be used to enclose the storage and transport apparatus.

In addition, it may be desirable to control and monitor the temperature of the BAO during transport. The tertiary shipping container may be packaged with thermal insulating gel packs or the like, such as are commercially available from Packaging Products, Inc. of New Bedford, Mass.

The shipping containers themselves may be insulated, and it may be desirable to include an inversion indicator or temperature recorders to ensure proper temperature handling of the BAO. Insulated containers with inversion indicators are commercially available (e.g., EnduroTherm insulated container, Source Packaging of New England, Warwick, R.I.). Any suitable temperature probe may be used (e.g., Data Trace, Mesa Laboratories, Inc., Wheat Ridge, Colo.).

The shipping container must be durable and able to adsorb the shock of being dropped or other movement during shipping so as to protect the BAO from damage. Insulated shipping containers having thick layers of insulation (1–3 inches) are useful for adsorbing shock to the container during shipping.

The invention is further illustrated by the following example, which is not to be viewed as limiting in any way.

EXAMPLE

The apparatus for storage and transport of a BAO was assembled and comprised a media storage container holding approximately 80 ml of a suitable fluid media. The media storage container had a well, or low spot, positioned away from the center of the base of the media storage container. The media storage container was made from an optically clear polycarbonate material and formed by injection molding, using a mold machined from stainless steel or aluminum.

The media storage container had an outer diameter of approximately 3.78 inches and a sealing rim of 0.1925 inches wide. The inner diameter of the media storage container was approximately 3.40 inches and could be filled with about 80–100 mls of the media to immerse the BAO. The thread of the storage container was an SP-400 finish as described by the Plastic Bottle Institute, Technical Committee, a division of the Society of Plastics Industry Incorporated. Furthermore, the thread finish identification was size 100 and preferably a modified buttress thread.

The securing means was comprised of a number of posts and prongs placed perpendicular to the bottom surface of the media storage container. The height of the posts were such that the tops of the posts would extend up to the bottom of the sealing means. This further prevented the BAOs from undue movement within the storage container.

The posts and prongs were an integral part of the base and were formed by injection molding. The prongs had a slotted, tapered section approximately 0.026 inches wide in order to pinch the BAO tether section which was 0.030 inches in diameter, as it was slid into place. The polycarbonate material from which the posts and prongs were made, allowed for the tether to be held firmly and was tough enough so as not to break under the load.

The posts and prongs were positioned along the bottom of the container such that the media container could securely hold a 5 cm active length and/or a 7 cm active length BAO such that the cell-containing membrane portion of the BAO would be in the center of the media storage container. The BAOs used in this example had compressible hollow silicone tethers attached to one end of the BAO with an approximate outer diameter of 0.030 inches.

The sealing means used was in the form of a threaded lid which engaged mating threads on the bottom on top of the media storage container. The thread of the lid was a #100–400, 5TPI, modified buttress thread as described by the Closure Manufacturers Association specifications. The lid was lined with a compressible silicone elastomer material to aid in the formation of a fluid tight seal. This liner was made from a layered construction by cocurrent extrusion methods of silicone between a layer of a polypropylene film and a layer of FEP. The silicone was 0.040–0.100 inches thick and the films were 0.005–0.010 inches thick. The liner was fixed to the lid by ultrasonic welding. The inner layer of the liner was made from the same material as the lid, specifically polypropylene, to facilitate ultrasonic welding. The ultrasonic welding of the liner was achieved by direct bonding energy to the materials. Six weld spots, each 0.375 inches in diameter, were applied symmetrically around the cap in order to firmly bond the liner in place.

The media storage container had a 90° knife edge approximately 0.010 inches high around the outer rim, which cut into the compressible FEP and silicone portions of the lid liner to aid in the formation of a fluid tight seal. The bottom of the media container had a key mechanism which fit into a mating base and/or a base plate. The key mechanism, a 10° offset tab, allowed for alignment of the pierceable septum over the media well and also for alignment of the septa of the secondary container over the septa of the media storage container.

The apparatus of this example contained both a media exchange means and a gas exchange means. These exchange means comprised self-sealing silicone septa.

The media was exchanged by inserting a needle through a silicone septum approximately 0.125 inches thick and 0.550 inches in diameter, followed by aspiration and removal of the media. Fresh media was introduced with another needle through the same silicone septum. A cap fitting was used to cover the septa during storage.

Gas exchange was performed by inserting a hollow needle through the second septum. The needle contained a 0.22 micron Teflon filter in a polypropylene housing held onto the needle with a leur fitting. The gas exchange septum further comprised a stop member which limited the extent to which the needle could travel into the interior of the media storage container. For longer term storage, the device is placed in storage incubators with the needle inserted through the septum. If the device is to be shipped, the needle was removed during the brief shipping period and the septum self-seals to provide a fluid-tight seal.

The materials used for the fabrication of the apparatus were polycarbonate, polypropylene, and silicone, and are completely disposable, and were not reused. These materials were selected since they can withstand gamma irradiation sterilization methods, sufficiently durable to withstand the rigors of shipping and are sufficiently non-toxic to living cells as to not produce appreciable detrimental effects to the BAOs. The materials were all USP Class 6 tested.

The apparatus further comprised a secondary container which surrounded the sealed media storage container. The secondary container had gas and media accessing means, both of which were self-sealing septa aligned over the self-sealing septa of the media storage container. In this example, the secondary container is similar to the media storage container, in that it had a similar lid construction, similar self-sealing septa for accessing the interior of the media storage container. The secondary container also had a humidity exchange means of 0.22 micron nylon membrane having a diameter of 0.312 inches. Accessing the interior of the media storage container was accomplished by aligning the septa of the secondary container over the septa of the media storage container such that a needle may be inserted through the septum on the secondary container and through the septum on the primary container to provide media or gas exchange.

The apparatus used in this example was assembled (threaded lids disengaged) including lid liners, septa, snap fittings, and secondary container base ring and placed in bags for sterilization by gamma irradiation. The sterile units were then place in a sterile hood where the BAOs were loaded.

BAO Loading Procedures

Figure 4:
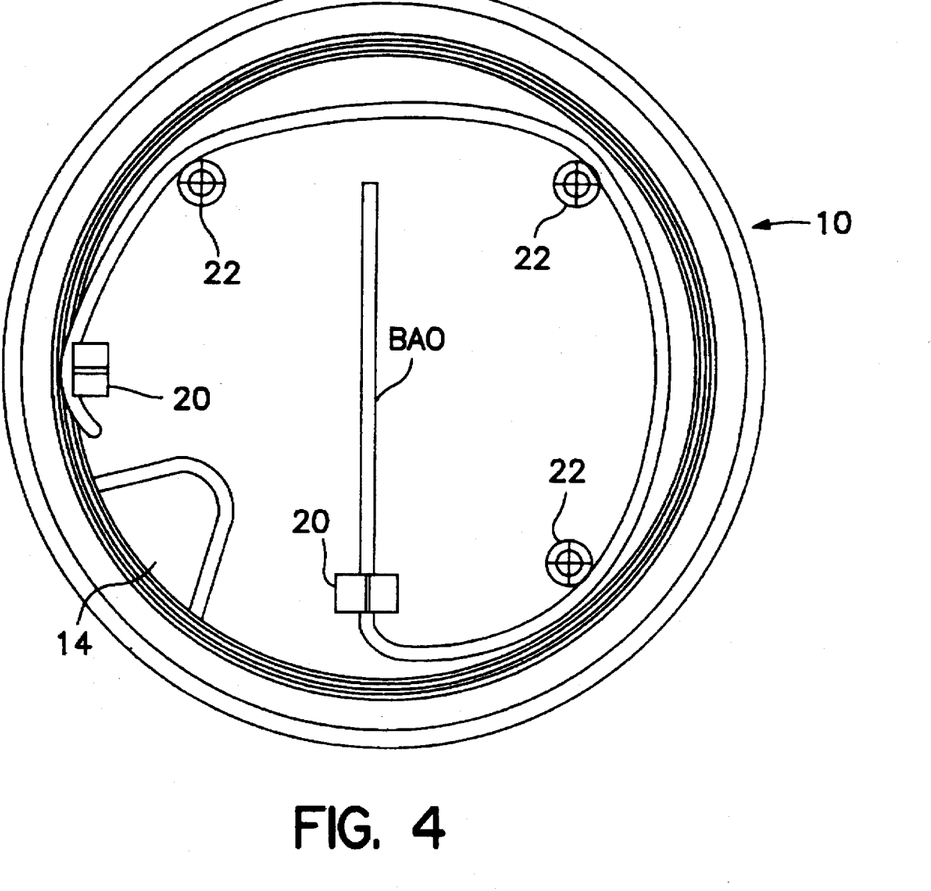
FIG. 4 shows a top view of media storage container 10 and securing means 20 holding a BAO.

The loading of the BAO was performed according to the following procedures:

(1) the media storage container was placed on the base plate such that the mating tabs on the base plate fit within the slots on the bottom of the media storage container;

(2) 10 mls of the selected media was added into the media storage container in order to wet the bottom of the container;

(3) the BAOs were then loaded, as shown in FIG. 4, by placing the thin, cylindrical BAOs in the center of the media storage container;

(4) the silicone tether was inserted in into the prongs and then wrapped around the posts;

(5) the media storage container was then tightly sealed with the threaded lid using the base plate to hold the container so that the knife edge cut into the lid liner;

(6) the alignment of the media exchange means over the media well of the media storage container was then visually confirmed;

(7) the sealed media storage container with the BAO inside was then placed into the secondary container on top of the slotted mating base, such that the tabs of the mating base fit within the slots of the key mechanism on the bottom of the media storage container;

(8) the secondary container was then tightly sealed with the threaded lid so that the knife edged lid cut into the lid liner;

(9) the gas exchange needle and the 22 micron filter-housing were then placed through the gas accessing septum of the secondary container and then through the gas exchange septum of the media storage container;

(10) the media exchange needle was then placed through the gas accessing septum of the secondary container and then through the gas exchange septum of the media storage container, such that the tip needle enter the media well; and (11) the remaining 70 ml of media is then added through the media exchange needle, thus filling the media storage container.

Transportation and Unloading Procedures

The loaded, BAO-containing apparatus was then delivered to the implantation destination according to the following procedures:

(1) the gas exchange needle was removed from the media storage container;

(2) the apparatus was placed in an insulated and durable tertiary packaging box having heat packs and temperature monitoring devices;

(3) the apparatus was then shipped to the implantation destination via routine methods of transportation;

(4) at the implantation destination, the apparatus was removed from the shipping package and the lid of the secondary container was disengaged so that the sterile, loaded and sealed media storage container could be introduced to the sterile surgical field;

(5) once inside the sterile field, the lid on the media storage container was disengaged; and (6) the BAO was then removed from the media storage container by unwrapping the BAO's tether from the posts and disengaging the tether from the prongs.

Pre-Implantation Testing Procedures

Prior to implantation into patients, BAOs generally should be shown to be functional and sterile. This testing can require holding periods of approximately 17–24 days to complete. During this time period, it may be necessary to change the media to maintain cell viability. For example, as described above, where the BAOs contain bovine adrenal chromaffin cells, it is necessary to replenish the medium after about twelve days. After media exchange, a short three day hold is performed to ensure BAO sterility. The BAOs are then shipped after day 15, but up to day 20. At day 20, the cells must be fed again followed by another short three day hold.

Product Evaluation Procedures

1. Sterility Testing

The BAOs were loaded and media exchanged as described above and the BAOs were stored in the apparatus for 29 days. The sterility was evaluated throughout using USP sterility evaluations, and the devices were found to remain sterile.

2. Leak-Proofness Testing

The sealed media storage container and sealed secondary container were evaluated for air and fluid tight seals. The air-tight test was performed by the addition of 1–3 psi of compressed nitrogen, and evaluated for maintained of the pressure over time. The devices were found to remain air-tight at 1–3 psi of pressure for extended periods of time. The fluid-tight seal was assessed by adding media, inverting the containers, and swirling the media inside the containers for extended periods of time. The devices were found to remain liquid-tight.

In addition, the devices were shipped unattended from Rhode Island by a common carrier to a site in Virginia. The devices were returned and there was no evidence of violation of the liquid-tight seal.

Drop testing 10–20 feet vertical was also performed in order to ensure that damage would not occur during transport.

3. Toxicity Testing

The toxicity of the fabrication materials to was tested by evaluating the output of BAO for analgesic substances after being stored for 29 days, including media replacement at days 12 and 20 as described above. In addition, the cells used in BAO's were directly placed on the materials and similarly evaluated for the output of active substances and cellular morphology changes.

The materials were found to be non-toxic to neither the cells nor the BAOS. The analgesic substances were unchanged by exposure to the materials.

We claim:

1. A bioartificial organ storage and transport apparatus, comprising:
   (a) a media storage container having a base, sides extending from the base, and a securing means attached therein for securing the bioartificial organ to the media storage container;
   (b) a cap which mates with the media storage container to form a fluid-tight seal, wherein the bioartificial organ is submerged in fluid media;
   (c) a gas exchange means positioned through the sides of the media storage container or through the cap;
   (d) a secondary container having a base and sides extending from the base and capable of enclosing the media storage container when mated to the cap;
   (e) a secondary cap which mates with the secondary container; and
   (f) wherein the secondary container or secondary cap comprises gas accessing means for accessing the gas exchange means, said gas accessing means is positioned through the sides of the secondary container or through the secondary cap.

2. A bioartificial organ storage and transport apparatus, comprising:
   (a) a media storage container having a base, sides extending from the base, and a securing means attached therein for securing the bioartificial organ to the media storage container:
   (b) a cap which mates with the media storage container to form a fluid-tight seal, wherein the bioartificial organ is submerged in fluid media:
   (c) a media exchange means positioned through the sides of the media storage container or through the cap:
   (d) secondary container having a base and sides extending from the base and capable of enclosing the media storage container when mated to the cap;
   (e) a secondary cap which mates with the secondary container; and
   (f) wherein the secondary container or secondary cap comprises media accessing means for accessing the media exchange means, said media accessing means is positioned through the sides of the secondary container or through the secondary cap.

3. The apparatus of either claim 1 or 2 further comprising a mating base inside the base of the secondary container that mates with a key mechanism on the base of the media storage container.

* * * * *